United States Patent [19]

Rall et al.

[11] Patent Number: 5,165,793
[45] Date of Patent: Nov. 24, 1992

[54] DEW POINT MEASURING METHOD AND APPARATUS

[75] Inventors: Dieter L. Rall, Los Gatos; Kurt Ladendorf, San Jose, both of Calif.

[73] Assignee: Lustron Corporation, Santa Clara, Calif.

[21] Appl. No.: 775,332

[22] Filed: Oct. 11, 1991

[51] Int. Cl.$^5$ .............................................. G01N 25/68
[52] U.S. Cl. ......................................... 374/28; 374/16
[58] Field of Search ............................... 374/16, 27, 28

[56] References Cited

U.S. PATENT DOCUMENTS 4,579,462  4/1986  Rall et al. .............................. 374/28

FOREIGN PATENT DOCUMENTS 0709988  1/1980  U.S.S.R. .................................. 374/28

OTHER PUBLICATIONS

Rall, Dieter; "Development of a High Temperature Dew-Point Measuring Apparatus Based on Differential Heat Flow Measurements"; *Drying '86*, vol. 2, Mujumdar, ed.; Washington: Hemisphere Publishing Corporation, 1986.
Rall, Dieter; "Performance of a New Heat-Flux Based Dew-Point Sensor In High Temperature Dirty Drier Environments", Sep. 15-17, 1987, presented at the Sensors Conference/Expo, Detroit, Mich.
TransMet Engineering, Inc., "Precise Moisture Control: High Temperature Dew Point Measurement", (undated), Anaheim, Calif.

*Primary Examiner*—William A. Cuchlinski, Jr.
*Assistant Examiner*—W. Morris Worth
*Attorney, Agent, or Firm*—Majestic, Parsons, Siebert & Hsue

[57] ABSTRACT

Apparatus and method for determining and tracking dew point temperatures. The dew point is measured by lowering the temperature of a condensing surface that is associated with a heat flow sensor. After condensation occurs the heat flux across the condensing surface is maintained at a preselected value by adjusting the temperature of the condensing surface. As long as a positive heat flow is maintained into the condensing surface, the temperature of the condensing surface is maintained at a slightly lower temperature than the saturation temperature which is by definition the dew point. The dew point temperature calculation is based on the relationship that when condensate forms on the condensing surface, the temperature of the condensing surface approaches the dew point temperature as the heat flow rate across the condensing surface approaches zero, i.e., at adiabatic conditions.

9 Claims, 1 Drawing Sheet

DEW POINT MEASURING METHOD AND APPARATUS

FIELD OF THE INVENTION

The present invention relates generally to an apparatus for measuring the dew point temperature of a gas, and in particular, to an apparatus for measuring the dew point temperature of hot, dirty, and contaminated industrial gases. The apparatus is effective over wide temperature and humidity ranges.

BACKGROUND OF THE INVENTION

The dew point is the temperature at which air with a given moisture content becomes saturated. This measurement is accomplished by artificially lowering the temperature of a surface and then noting the temperature at which moisture first condenses.

Many types of dew point sensors are known to the art. Some dew point sensors are capacitive and resistive devices and employ moisture-sensitive material to sense condensation. The moisture-sensitive material is formed into a condensation surface on the dew point sensor, and heat is slowly removed from the sensor until condensation begins. The moisture-sensitive material reacts to the presence of the moisture of condensation, for example by changing resistance. The temperature of the sensor is continuously monitored, and when this change of resistance is detected the temperature is recorded.

Another prior art form of dew point sensor is a condensing mirror type provided with a reflective surface. When the temperature of the reflective surface is reduced to the dew point temperature, condensation takes place. The moisture of condensation is detected either by visual inspection or by the use of a photocell or other light-sensitive device that responds to the change in reflectivity caused by the presence of moisture.

Unfortunately, none of the dew point measuring instruments just described is able adequately to satisfy the requirements for use in industrial processes. The high temperatures that occur in industrial processes damage the components used in many sensors, and the contaminants often found in such processes alter the absorption properties of many moisture-sensitive sensors and cloud the reflecting surfaces of reflector type sensors. Moreover, those devices have a limited range of operation and are limited to temperatures below 200° F. Furthermore, capacitive and resistive devices provide indirect dew point measurements. Thus, these instruments must be calibrated for specific relative humidities from which the dew point temperature is calculated.

Various other methods of achieving accurate measurements under industrial process conditions have been attempted. One such device is disclosed in Rall et al., U.S. Pat. No. 4,579,462, issued Apr. 1, 1986, which describes a dew point measuring apparatus that is characterized by a heat flow sensor which, in one embodiment, comprises a condensation surface and an embedded differential thermopile. The heat flow sensor measures the flow of heat into the surface rather than the temperature of the surface. It senses the exothermic release or endothermic absorption of heat as moisture condenses on or evaporates from the surface at the dew point temperature. When the apparatus is used to determine the relative humidity of a gaseous atmosphere, the temperature of the sensor is slowly lowered until the dew point of the atmosphere is reached. As soon as condensation begins, heat of condensation is released from the condensate and flows into the condensation surface. The heat flow sensor responds to this heat flow, thereby permitting the determination of the atmosphere's dew point, and hence of its relative humidity.

In practice, the above described apparatus requires a pair of heat flow sensors mounted adjacent a heat sink. A coolant is circulated through the heat sink to slowly reduce the temperature of the sensors. A heater is provided which is actuable to raise the temperature of the sensors. By actuating and deactuating the heater the temperature of the sensors can be cycled up and down through the dew point of a gas or atmosphere under test, thereby permitting the atmosphere's dew point to be tracked. One of the sensors is kept at a slightly higher temperature than the other, and the output signals from the two sensors are compared, as by connection in series opposition. A stream of gas under test is passed over the sensors. A relatively sudden change or imbalance in the signal from the oppositely electrically connected sensors occurs as moisture condenses on the cooler sensor and the exothermic heat of condensation is released. The surface temperature of the cooler sensor at that instant is the dew point of the gas.

Although the dual heat flow sensor device is better suited than capacitive and resistive devices for measuring gases with contaminants, it nevertheless has limitations. Its principal drawback is that with dual heat flow sensors, it is difficult to calibrate over wide dew point temperature and relative humidity ranges.

SUMMARY OF THE INVENTION

It is the object of the present invention to provide a method and device for dew point measurements that can be used in harsh environments containing dust or other contaminants.

It is another object to provide a sensitive device for direct dew point measurements that can operate over wide ranges in temperatures and relative humidities.

These and other objects are accomplished with the inventive method and device for measuring and tracking dew point temperatures. The dew point is measured by lowering the temperature of a condensing surface that is associated with a heat flow sensor. The heat flux across the condensing surface is maintained at a preselected value by adjusting the temperature of the condensing surface. As long as a positive heat flow is maintained into the condensing surface the temperature of the condensing surface is maintained at a slightly lower temperature than the saturation temperature which is by definition the dew point and is also the temperature of the condensate layer and air interface. The dew point temperature calculation is based on the relationship that when condensate forms on the condensing surface, the temperature of the condensing surface approaches the dew point temperature as the heat flow rate across the condensing surface approaches zero, i.e., at adiabatic conditions.

In one embodiment, the thermal balance is maintained by employing a single heat flow sensor which is imbedded in the face of the thermally conductive body. The sensor monitors the rate of heat transfer at the condensing surface. The sensor also generates a signal which is bidirectional, that is, heat flow from the gas into the condensing surface generates a positive signal while heat flow from the condensing surface to the gas generates a negative signal. Cooling coils are suitably arranged so as to lower the temperature of the condensing surface.

In using the device, cooling is continuously provided by a heat exchanger with sufficient capacity to cool the temperature of the condensing surface below the dew point regardless of the heating by the air sample passing over the sensor. This insures that the heat flux will always be into the sensor surface. The temperature of the condensing surface is then increased until the heat flux reaches a preselected rate by means of a heater placed between the cooling and the sensor surface. Thereafter, should the heat flux into the condensing surface exceed the preselected rate q', signals from the sensor to the controller will actuate an electric heater, thereby raising the temperature of the condensing surface and reducing the heat flow to q', the preselected value.

Similarly, if the dew point decreases which reduces the heat flux into the conductive body, signals from the heat flow sensor will (partially or fully) deactivate the heater. This allows the condensing surface to be cooled so that it can track the new dew point and reduce the heat flux to the predetermined rate q'. In normal operation, coolant continues to circulate throughout the measurement. The heater power is varied as a function of the heat flow sensor signal to adjust and maintain the net heat flux to the condensing surface at the preselected flux q'. Again, this assures that the condensing surface, which is exposed to the vapor-air mixture, is always in a fixed thermal balance with the condensate which accumulates on the condensing surface. A temperature sensor at the surface of the heat flow sensor is kept at a direct relationship to the saturation or dew point temperature at the air-condensate interface.

The inventive device can be used in harsh environments wherein dust or other contaminants would normally interfere with prior art devices. For instance, with condensing mirror dew point, resistivity, or salt solution devices, the deposition or condensation of contaminants on the sensor surfaces adversely affect the accuracy of these devices. Furthermore, the inventive device can function at much higher environmental gas, e.g., air, temperatures vis-a-vis prior art devices. This is particularly important in working with high air temperature drying and processing ovens and power plant exhaust gases.

DESCRIPTION OF THE PREFERRED EMBODIMENTS

Many industrial applications involve processes in which a condensable vapor is being carried through the system by a gas that remains uncondensed and chemically unaltered throughout the process. Solvent recovery, air conditioning, drying, and humidification are examples. The "permanent" gas component in such a process is commonly referred to as the carrier gas to describe its function. In any such system, if the partial pressure of the vapor is less than its equilibrium vapor pressure, the carrier gas is not saturated with the vapor, and whatever vapor is present is in the superheated condition. Carrier gas absolutely devoid of condensable vapor is said to be bone dry. The relative saturation of the vapor-gas mixture is defined as the percentage ratio of the partial pressure of the vapor to its equilibrium vapor pressure at the temperature of the system. Water vapor is so commonly encountered as the condensable vapor that a special terminology has been devised for it in which the word "humidity" is substituted in place of "saturation".

The inventive device and method are applicable to vapor-carrier gas systems in general, although the description hereinbelow will focus on water vapor in air systems.

Figure 1:
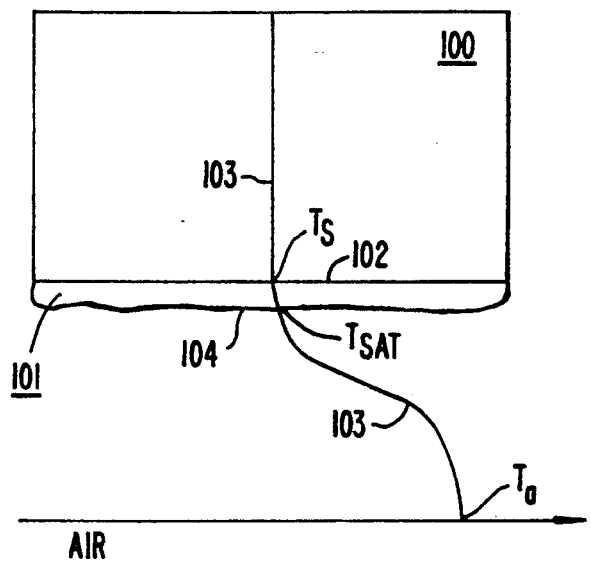
FIG. 1 shows the temperature profiles of a thermally conductive body, condensate, and gas.

As shown in FIG. 1, when moist air that has a free stream temperature of $T_a$ comes into contact with a thermally conductive body 100, condensation forms if the temperature of the body is at or below the dew point. The condensate film 101 that forms has average thickness $\delta$ and thermal conductivity $K_w$. If the condensing surface 102 of the thermally conductive body is kept at a thermal balance with the condensate layer, such that a positive flow of heat into the condensing surface is maintained, a temperature gradient represented by curve 103 is established. So long as the temperature $T_s$ of the condensing surface is maintained at or below the dew point, condensate remains. (As is apparent, the temperature of the conductive body at the condensate surface interface is also at $T_s$.) The condensate film 101 has an insulating effect so that the film surface 104 temperature, $T_{SAT}$, is higher than that of the condensing surface 102. By definition, $T_{SAT}$, the temperature at the water vapor interface, is the dew point temperature.

The heat flux (q) into the conductive body 100 can be represented by the following formula:

$$q = \frac{K_w}{\delta}(T_{SAT} - T_S) \qquad \text{FORMULA I}$$

or, $$T_{SAT} = T_S + (q \times \delta)/K_w \qquad \text{FORMULA II}$$

It is apparent that by maintaining near adiabatic conditions of low constant heat flux (q) into the body surface, condensation at the condensing surface is assured. Furthermore, the system is designed to respond to fluctuations in the gaseous environment. For example, should the dew point temperature drop, e.g., if the relative humidity decreases, the concomitant decrease in the heat flux is detected which triggers a reduction of power to the heater and thus allows for additional cooling. The temperature of the conductive body is thus adjusted to be slightly below the new dew point temperature which in turn restores the heat flux to the preselected value. Conversely, if the dew point rises, the temperature of the condensing surface is raised in order to maintain the constant heat flux. In this fashion, the condensing surface temperature $T_s$ will track the dew point temperature $T_{SAT}$.

Figure 2:
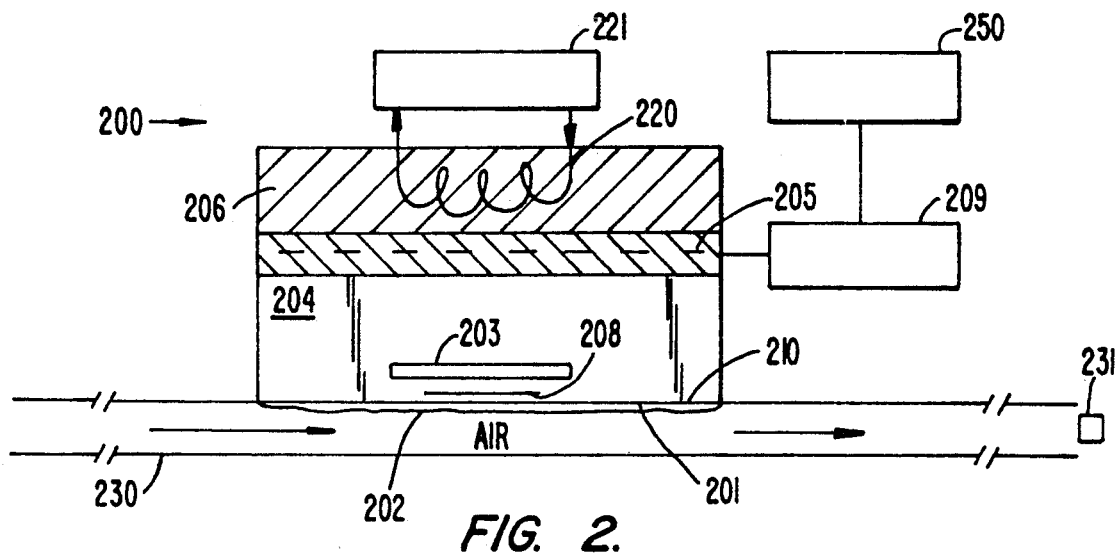
FIG. 2 is a schematic of one embodiment of the inventive device.

Illustrated in FIG. 2 is a device 200 for measuring the dew point temperature by maintaining the condensing surface 210 at a predetermined thermal balance with the condensate 201. The thermal balance is maintained by employing a heat flow sensor 203 which is imbedded in the face of the thermally conductive body 204. The latter is constructed of aluminum, copper, or other suitable material. The sensor monitors the rate of heat transfer at the condensing surface. The particular form of the heat flow sensor is not critical to the present invention so long as it is capable of sensing the heat flow through the condensing surface. A thermopile is a preferred heat flow sensor. The sensor provides a self-generated signal which is bidirectional, that is, heat flow from the water layer into the condensing surface generates a positive signal while heat flow from the condensing surface to the water layer generates a negative signal. The temperature of the gas-condensate interface 202 is by definition the saturation or dew point temperature.

Cooling coils 220 are suitably arranged within cooling block 206 so that circulating of a coolant, e.g. water, through the coils operates to continuously lower the temperature of the cooling block. The coolant is supplied by coolant source 221.

In using the device, the temperature of the condensing surface is always maintained below the dew point by the coolant and by controlling the power to the heater 205 to maintain a positive heat flux into the condensing surface. The temperature of the condensing surface is thus always kept at the required temperature to maintain the preselected heat flux $q'$. The heat flux is measured by the heat flow sensor 203 that is connected to heat controller 209. Thus, if the heat flux into the condensing surface should exceed a preselected $q'$, signals from the sensor to the controller will actuate the electric heater 205 which is situated between the thermally conductive body 204 and the cooling block 206. The leads connecting the heat flow sensor and the controller are not shown. Heat flows from the activated heater into the cooling block and the conductive body. The net effect is that the temperature of the body and condensing surface is raised thereby reestablishing the heat flow at $q'$.

Similarly, if the dew point decreases which reduces the heat flux into the conductive body, signals from the heat flow sensor will (proportionally or fully) deactivate the heater. This allows the conductive body to be cooled to a point just below the new dew point so that the heat flux returns to the predetermined rate $q'$. In normal operation, coolant continues to circulate throughout the measurement. This assures that the condensing surface, which is exposed to the vapor-air mixture, is always in a fixed thermal balance with the condensate which accumulates on the condensing surface. A temperature sensor 208 (such as a platinum RTD) at the surface of the heat flow sensor is kept at a direct relationship to the saturation or dew point temperature at the air-condensate interface.

A microcontroller 250 can be employed to regulate the heat controller. Moreover, the microcontroller can calculate and monitor the dew point temperature from the output signals from the heat flow and temperature sensors.

To maintain near-adiabatic conditions, the preselected constant heat flow rate $q'$ is set as low as practicable. For dew point measurements of air over an approximate temperature range of 100 to 300° F. and an approximate relative humidity range of 10 to 90%, the value of $q'$ can range from 100 to 250 BTU per square foot per hour.

For many applications, water can be used as a coolant. However, for many industrial applications with low dew point ranges, other coolant such as refrigerator glycol, may be required.

Dew point temperature measurements with the inventive device 200 were compared with dew point temperatures calculated from wet bulb/dry bulb measurements and calibrations using steam tables. It was found that the condensing surface temperature $T_S$ follows the dew point $T_{SAT}$ within three to four degrees Fahrenheit. This offset was found to be relatively constant. In calculating the true dew point, this discrepancy should be taken into account.

As described above, the value of the preselected heat flux $q'$ controls the signal level from the heat flow sensor required to trigger the heating and cooling cycles. Moreover, the thickness $\delta$ of the condensate layer depends, in part, on the value of $q'$ since as more condensate forms the temperature gradient between $T_S$ and $T_{SAT}$ increases. Thus, to avoid excessive condensation, $q'$ should be kept at a minimum. To clean off excessive condensate, air is periodically blown over the condensing surface by diverting the airflow from the eductor 231 back over the sensor for a few seconds every minute or so. This assures that a clean condensate layer can reform. The microcontroller is designed to hold the dew point reading during the condensate layer reformation period. However, practical concerns notwithstanding, with the inventive device and method, there is no inherent limitation with regard to the temperature and relative humidity ranges to which the invention is applicable.

As shown in FIG. 2, the condensing surface of the inventive device is positioned in a sample flow channel 230 so the gas comes into contact with the surface. Air sample is drawn through by air eductor 231 or other device. The sample flow channel, for instance, can be connected to an industrial processing chamber in order to monitor the relative humidity in the chamber. Samples of gas are continuously extracted from the processing chamber through the sample flow channel. The samples are then recycled into the processing chamber or discharged.

Figure 3:
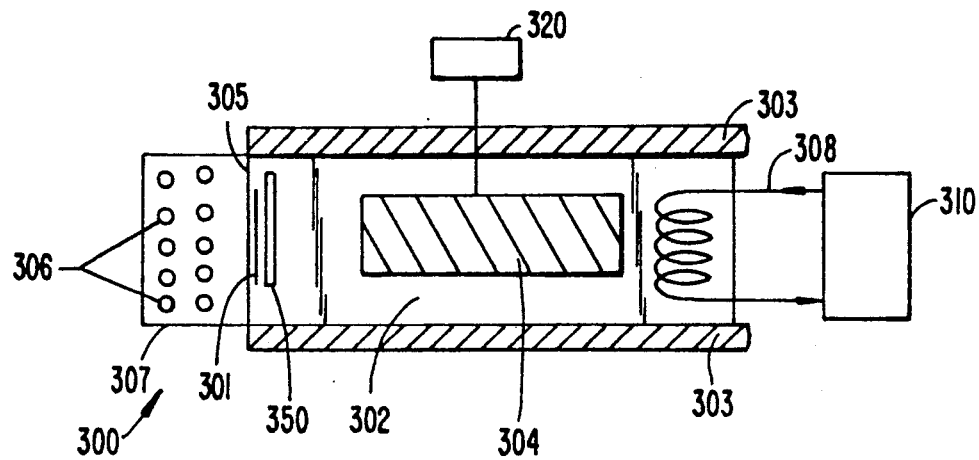
FIG. 3 is a schematic of an embodiment of the inventive device in which heat flow and temperature sensors are attached to the end of a probe.

FIG. 3 shows another embodiment of the invention in which device 300 is positioned at the end of a probe. In this embodiment, the thermally conductive body 302 is covered by insulating layers 303 which also protects the probe in harsh environments. Temperature change means for altering the temperature of the conductive body, including cooling coils 308 and an electrical resistance heating element 304, are embedded in a portion of the conductive body. Coolant is supplied by coolant source 310 and heating is monitored by heat controller 320. Gas samples diffuse through perforations 306 in the convective draft shield 307 which covers the condensing surface 305. Temperature sensor 301 measures the temperature $T_S$ of the condensing surface and heat flow sensor 350 measures the heat flux across the surface. This device is particularly well suited for measuring the dew point at different locations within a large vessel or for use as a portable unit for field testing.

It is to be understood that while the invention has been described above in conjunction with preferred specific embodiments, the description and examples are intended to illustrate and not limit the scope of the invention, which is defined by the scope of the appended claims.

It is claimed:

1. A device for measuring and tracking the dew point temperature of a gas comprising:
   a thermally conductive body having a condensing surface onto which condensate forms;

means for cooling the thermally conductive body below the dew point temperature of said gas;

a heat flow sensor positioned in the thermally conductive body in a manner to measure the heat flow through the condensing surface and to generate an output signal proportional to the rate of said heat flow;

a temperature sensor to measure the temperature of said condensing surface and to generate an output signal proportional to the temperature of said condensing surface;

temperature change means responsive to the signal from the heat flow sensor to change the temperature of the thermally conductive body so that heat flows into the condensing surface at a preselected heat flow rate;

and means responsive to signals from said heat flow sensor and said temperature sensor for calculating the dew point temperature of said gas.

2. The dew point and tracking device as defined in claim 1 further comprising means for removing condensate from said condensing surface.

3. The dew point measuring and tracking device as defined as in claim 1 wherein the cooling means comprises a cooling coil and the temperature change means a resistive heater, both said cooling coil and heater being in thermal association with the thermally conductive body, wherein the heat flow sensor comprises a thermopile, and wherein the temperature sensor comprises a platinum RTD.

4. The dew point measuring and tracking device as defined in claim 3 further comprising a sample flow channel which defines a flow path for the gas.

5. The dew point measuring and tracking device as defined in claim 3 further comprising a perforated convective draft shield.

6. The dew point measuring and tracking device as defined in either claims 2, 3, 4, or 5 wherein said calculating means determines the dew point temperature $T_{SAT}$ by employing the relationship that $T_{SAT} = T_s + (g' \times \delta)/K_w$, wherein $\delta$ is the average thickness of the condensate, $K_w$ is the thermal conductivity of the condensate, $T_s$ is the temperature of the condensing surface, and $g'$ is the preselected heat flow rate.

7. A method for measuring and tracking the dew point of a gas comprising the steps of:
bringing the gas in contact with a surface of a thermally conductive body;

changing the temperature of the thermally conductive body to cause condensate to form on the surface of the thermally conductive body;

measuring the heat flow rate across the surface of the thermally conductive body when condensate has formed;

adjusting the temperature of the thermally conductive body until the heat flow into the conductive body reaches a preselected rate;

measuring the temperature of the surface of the thermally conductive body;

and calculating the dew point using the measured preselected heat flow rate and temperature.

8. The method as defined in claim 7 wherein the step of adjusting the temperature further comprises:
controlling the temperature of the thermally conductive body so that the heat flow remains approximately constant at the preselected flow rate;

the step of calculating the dew point comprises; and calculating the dew point $T_{SAT}$ by employing the relationship $T_{SAT} = T_s + (g' \times \delta)/K_w$, wherein $\delta$ is the average thickness of the condensate, $K_w$ is the thermal conductivity of the condensate, $T_s$ is the temperature of the thermally conductive body surface, and $g'$ is the preselected heat flow rate.

9. The method as defined in claim 8 further comprising the step of periodically removing condensate from the surface of the thermally conductive body.

* * * * *

UNITED STATES PATENT AND TRADEMARK OFFICE
CERTIFICATE OF CORRECTION

PATENT NO.   : 5,165,793
DATED        : NOVEMBER 24, 1992
INVENTOR(S)  : RALL ET AL.

It is certified that error appears in the above-identified patent and that said Letters Patent is hereby corrected as shown below:

Column 7:

| | |
|---|---|
| Claim 3, lines 25 and 26 | Insert the word --comprises-- between the phrases "temperature change means" and "a resistive heater," |
| Claim 6, line 2, column 8, | Replace "g'" with --q'-- |
| Claim 6, line 5, column 8, | Replace "g'" with --q'-- |
| Claim 8, line 31, column 8, | Replace "g'" with --q'-- |
| Claim 8, line 35, column 8, | Replace "g'" with --q'-- |

Signed and Sealed this

First Day of February, 1994

*Attest:*

BRUCE LEHMAN

*Attesting Officer*    *Commissioner of Patents and Trademarks*